(12) United States Patent
Jaime et al.

(10) Patent No.: US 12,308,104 B2
(45) Date of Patent: *May 20, 2025

(54) REMOTE ACCESS FOR MEDICAL DEVICE THERAPY

(71) Applicant: Tandem Diabetes Care, Inc., San Diego, CA (US)

(72) Inventors: Manuel Jaime, Solana Beach, CA (US); Josh Juster, San Diego, CA (US); Larkin Lowrey, Naples, FL (US); Geoffrey A. Kruse, San Diego, CA (US); Garrett Marin, San Diego, CA (US); Michael Michaud, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/397,808

(22) Filed: Dec. 27, 2023

(65) Prior Publication Data

US 2024/0127923 A1 Apr. 18, 2024

Related U.S. Application Data

(63) Continuation of application No. 17/573,705, filed on Jan. 12, 2022, now Pat. No. 11,869,650.
(Continued)

(51) Int. Cl.
*G08B 21/04* (2006.01)
*G16H 20/17* (2018.01)
*G16H 40/67* (2018.01)

(52) U.S. Cl.
CPC ............. *G16H 20/17* (2018.01); *G16H 40/67* (2018.01)

(58) Field of Classification Search
USPC ............ 340/539.12, 539.13, 539.22, 539.11, 340/539.14, 546, 568.1, 571,
(Continued)

(56) References Cited

U.S. PATENT DOCUMENTS

| 7,812,826 B2 | 10/2010 | Ording et al. |
| 7,924,271 B2 | 4/2011 | Christie et al. |

(Continued)

FOREIGN PATENT DOCUMENTS

| CA | 2771143 A1 | 4/2011 |
| CN | 102549544 A | 7/2012 |

(Continued)

OTHER PUBLICATIONS

Rezaeibagha et al., "Distributed Clinical Data Sharing Via Dynamic Access-Control Policy Transformation," Feb. 10, 2016.
(Continued)

*Primary Examiner* — Daniel Previl
(74) *Attorney, Agent, or Firm* — Morgan, Lewis & Bockius LLP

(57) ABSTRACT

Disclosed herein are systems and methods for remotely monitoring and/or controlling medical therapy of a patient. Embodiments of the current disclosure provide a remote monitoring and/or control architecture that can establish a predetermined set of permissions for real time monitoring of patient data and/or notifications and/or control of medical device therapy. The system can include permissions to determine who, how and when information and/or control is shared that can consider factors such as time, location and relationship with the patient.

11 Claims, 4 Drawing Sheets

Related U.S. Application Data

(60) Provisional application No. 63/136,422, filed on Jan. 12, 2021.

(58) Field of Classification Search
USPC ............ 340/572.1–572.9, 691.6, 3.63, 539.1
See application file for complete search history.

(56) References Cited

U.S. PATENT DOCUMENTS

| | | | |
|---|---|---|---|
| 8,209,606 | B2 | 6/2012 | Ording |
| 8,233,134 | B2 | 7/2012 | Van De Kerkhof et al. |
| 8,723,988 | B2 | 5/2014 | Thörn |
| 9,680,831 | B2 | 6/2017 | Jooste et al. |
| 9,943,597 | B2 | 4/2018 | Han et al. |
| 11,869,650 | B2* | 1/2024 | Jaime .................... G16H 40/67 |
| 2007/0156692 | A1 | 7/2007 | Rosewarne |
| 2010/0031202 | A1 | 2/2010 | Morris et al. |
| 2010/0180029 | A1* | 7/2010 | Fourman ................ G16H 10/60 |
| | | | 709/225 |
| 2011/0074710 | A1 | 3/2011 | Weeldreyer et al. |
| 2011/0074824 | A1 | 3/2011 | Srinivasan et al. |
| 2012/0084711 | A1 | 4/2012 | Duarte et al. |
| 2012/0089950 | A1 | 4/2012 | Tseng |
| 2012/0129139 | A1* | 5/2012 | Partovi .................. G16H 40/67 |
| | | | 434/262 |
| 2012/0147050 | A1 | 6/2012 | Dai et al. |
| 2014/0207486 | A1* | 7/2014 | Carty .................... G16H 40/67 |
| | | | 705/2 |
| 2015/0326570 | A1* | 11/2015 | Publicover ............. G06F 3/017 |
| | | | 382/117 |
| 2016/0300039 | A1* | 10/2016 | Burgio .................. G16H 10/20 |
| 2016/0357944 | A1* | 12/2016 | Iyer ........................ G16Z 99/00 |
| 2017/0181630 | A1* | 6/2017 | Mahalingam ............ G09B 5/02 |
| 2018/0182258 | A1* | 6/2018 | Deacon .................... G09B 5/02 |
| 2019/0180873 | A1* | 6/2019 | Kartoun .................. G16H 10/60 |
| 2020/0286400 | A1* | 9/2020 | Jackson ................. G16H 10/60 |
| 2021/0090730 | A1 | 3/2021 | Patel et al. |
| 2021/0217533 | A1 | 7/2021 | Heimerl |
| 2022/0193340 | A1 | 6/2022 | Patel et al. |
| 2022/0280104 | A1* | 9/2022 | Golay ................... G16H 10/60 |
| 2024/0257958 | A1* | 8/2024 | Pierson .................. H04W 4/02 |

FOREIGN PATENT DOCUMENTS

| | | |
|---|---|---|
| CN | 102609193 B | 11/2014 |
| WO | 2016115551 A | 7/2016 |

OTHER PUBLICATIONS

Westerman, "Hand Tracking, Finger Identification, and Chordic Manipulation on a Multi-Touch Surface," 1999.

Zhang et al., "Applying Multi-agent Systems Coordination to the Diabetic Healthcare Collaboration," Apr. 2018.

* cited by examiner

REMOTE ACCESS FOR MEDICAL DEVICE THERAPY

CROSS REFERENCE TO RELATED APPLICATIONS

This application is a continuation of U.S. patent application Ser. No. 17/573,705 filed Jan. 12, 2022, which claims benefit of U.S. Provisional Application No. 63/136,422 filed Jan. 12, 2021, both of which are hereby fully incorporated herein by reference.

FIELD OF THE INVENTION

The present invention relates generally to medical device therapy and, more particularly, to remote monitoring and/or control of medical device therapy.

BACKGROUND OF THE INVENTION

People with diabetes can treat the disease in a number of different ways, including with insulin pumps, insulin pens and regular injections with a syringe. Regardless of the method of treatment, it is important for the user to be able to track and review data relating to therapy in order to aid the user in better managing the user's diabetes. A number of different data management software programs, mobile applications, etc. have therefore been developed that enable a user to review therapy data.

Because the typical age of diagnosis of type 1 diabetes is 14 years old or younger, often a parent or other caregiver may need to monitor diabetes therapy provided to a child using one or more of the data management applications noted above. However, a parent or other regular caregiver cannot always be around a child or other patient to monitor and initiate therapy for the patient. Even if the parent or other caregiver can monitor the patient's therapy remotely, it may be difficult for the caregiver to contact a qualified individual who is with or near the patient to ensure any therapy needs are addressed. Similar considerations are also relevant to medical therapy for other conditions.

SUMMARY OF THE INVENTION

Disclosed herein are systems and methods for remotely monitoring and/or controlling medical therapy of a patient. Embodiments of the current disclosure provide a remote monitoring and/or control architecture that can establish a predetermined set of permissions for real time monitoring of patient data and/or notifications and/or control of medical device therapy. The system can include permissions to determine who, how and when information and/or control is shared that can consider factors such as time, location and relationship with the patient.

In an embodiment, a method of providing real-time access to a medical device includes storing a set of permissions for one or more followers of a user of a medical device, the set of permissions for each follower defining one or more times on one or more days during which a follower device of the follower may be provided access to the medical device. A location vicinity of the follower device can be determined at the times and days when the follower device may be provided access to the medical device. The follower device can be automatically provided with access to the medical device at the times and days when the follower device may be provided access to the medical device if the location vicinity of the follower device is in a predetermined location vicinity stored in the set of permissions. Access by the follower device to the medical device can be automatically prevented if the location of the follower device is not in the predetermined location vicinity and on days and times when the set of permissions does not indicate that the follower device may be provided access to the medical device.

In an embodiment, a method of providing real-time access to a medical device can include determining at a given time whether a follower device of a follower of a user of a medical device may be provided access to the medical device based on stored days and times when the follower device may be provided such access. A location vicinity of the follower device can also be determined at the given time. The follower device can automatically be provided with access to the medical device if the follower device may be provided access to the medical device at the given time and if the location vicinity of the follower device is in a predetermined location vicinity at the given time.

BRIEF DESCRIPTION OF THE DRAWINGS

The invention may be more completely understood in consideration of the following detailed description of various embodiments of the invention in connection with the accompanying drawings, in which.

Figure 1:
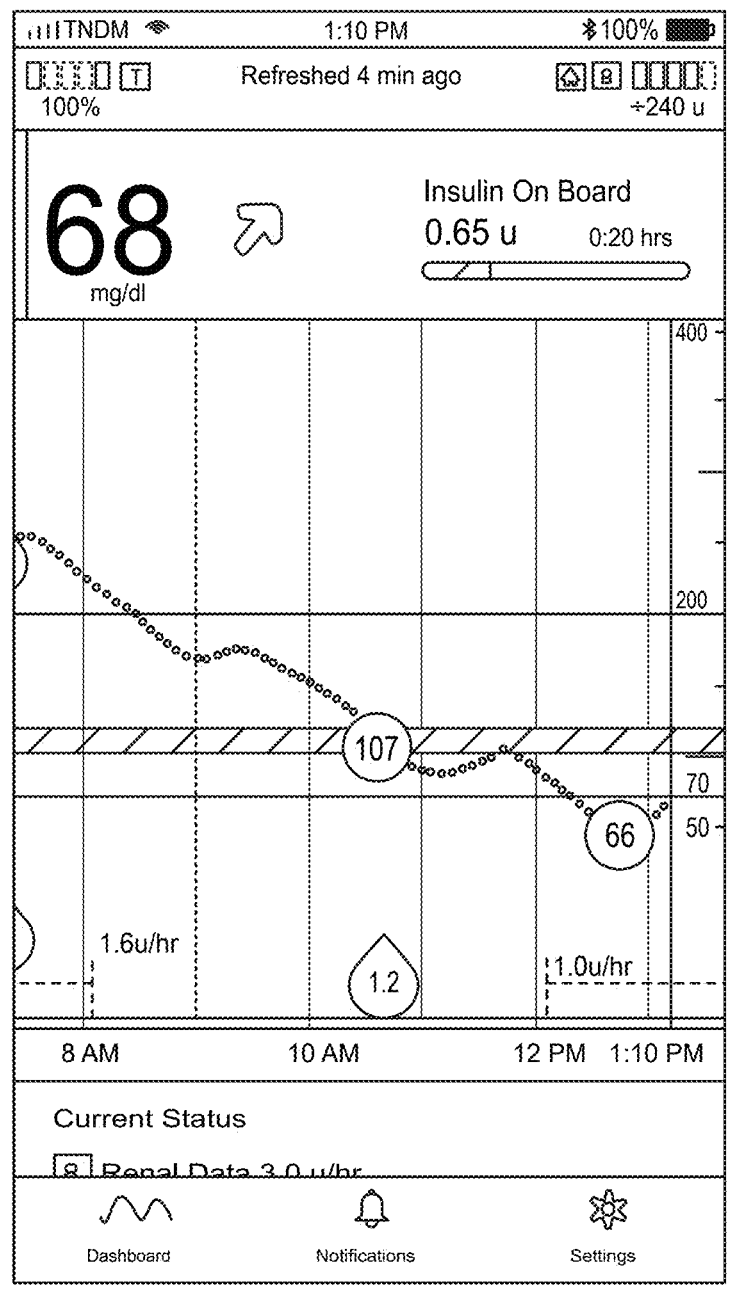
FIG. 1 is a user interface of a diabetes therapy monitoring application according to an embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 2:
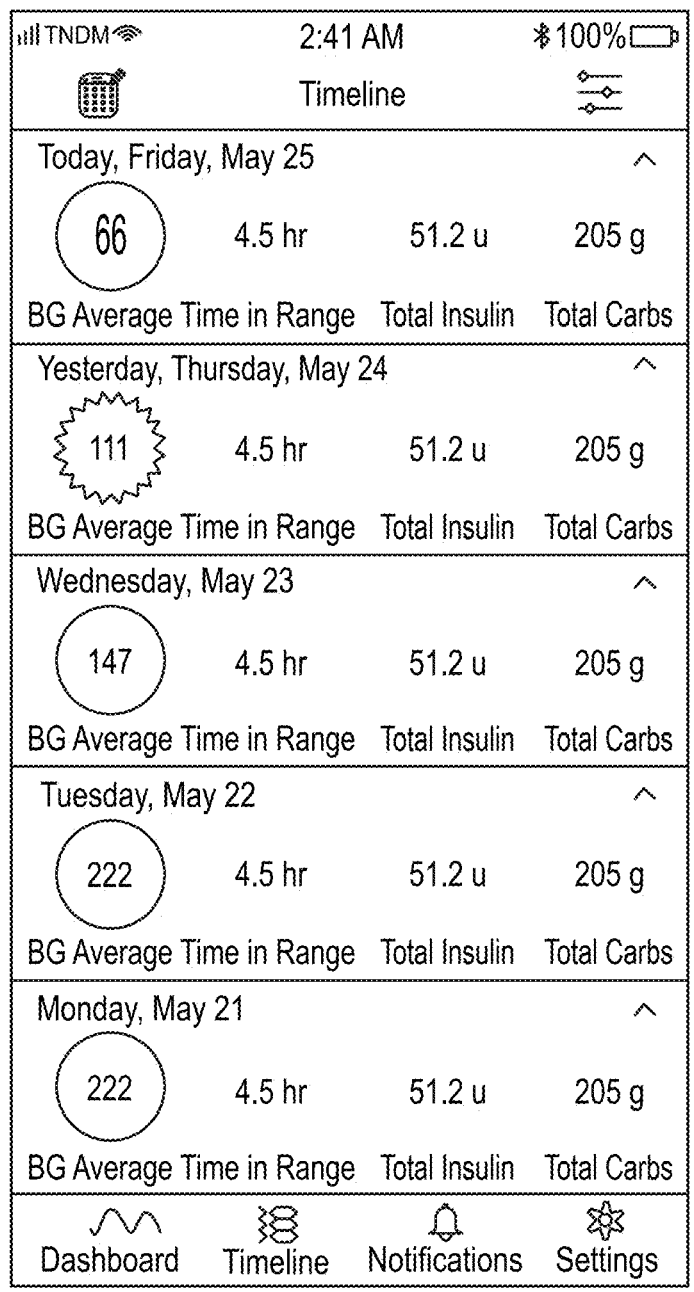
FIG. 2 is a user interface of a diabetes therapy monitoring application according to an embodiment.

Referring to FIG. 1, a user interface for real time monitoring of medical therapy such as diabetes therapy is depicted. In embodiments, the user interface can be displayed on a mobile device such as a smartphone operating a software application that receives and displays therapy data. In other embodiments, the user interface can be displayed on any other display device, such as, for example, a tablet computer, desktop computer or laptop. In the example of diabetes therapy, the therapy can be provided in any manner, including, for example, with an ambulatory infusion pump, an insulin pen and multiple daily injections. User interface can provide information on any number of aspects of therapy. For example, the disclosed interface directed to diabetes therapy depicts a current glucose level of the user, a glucose level trend arrow, a current level of insulin on board, an amount of battery life remaining for an insulin pump, an amount of insulin remaining in a reservoir of an insulin pump, historical glucose levels in graphical form including blood glucose measurement values, and basal rate and bolus amounts delivered to the user. FIG. 2 depicts another user interface for monitoring medical therapy such as diabetes therapy that can enable tracking of therapy over a number of previous days or other time period, including blood glucose daily averages, daily time in range, daily total insulin and daily total carbs consumed.

In addition to viewing of current and past data, diabetes and other medical monitoring applications can provide a number of additional functions. For example, applications can display alerts, alarms, reminders and other notifications. For example, in the context of diabetes therapy if a user has a current or predicted low or high glucose level, a low battery level of an insulin pump, a low amount of insulin remaining in an insulin pump, an infusion set, CGM transmitter or CGM receiver that is set to expire, etc. the diabetes monitoring application can provide a notification to a user of the application alternatively to or in addition to a notification provide by an insulin pump or other device of the patient. Such notifications can further include food events, exercise events, etc. In addition, a user may grant one or more parents, teachers or other caregiver access to the patient's data through the diabetes monitoring application such that any notifications can be provided to a plurality of individuals that may be in a position to aid the patient in addressing the reason for the notification.

However, a caregiver such as a teacher, school nurse, camp counselor, etc. will only be around a patient user a limited amount of time and on limited days such that a patient may not want to share and a caregiver does not need access to the patient's data and/or notifications at all times. Embodiments of the current disclosure therefore provide a remote monitoring and/or control architecture that can establish a predetermined set of permissions for real time monitoring of patient data and may also include an ability to remotely control some or all aspects of medical therapy for the patient. The system can include permissions to determine who, how and when information is shared that can consider factors such as time, location and relationship with the patient.

For example, for a child patient attending a summer camp, a parent may want to give a camp counselor or other supervisory adult access to the patient's data and/or notifications in order to be able to help the patient address any treatment issues. The parent may also want to give the supervisory adult an ability to control the medical therapy as needed. However, the counselor would not need constant access to the data or control, and it would be impractical for the parent to manually turn on and turn off access and/or control for the counselor repeatedly throughout the week. In addition, there may be days or times when the counselor is away from camp and therefore also would not need access to the patient's data or control of therapy. The remote monitoring and/or control architecture described herein can therefore enable the parent to set a conditional set of permissions for one or more individuals based on day, time and geographic location of caregiver such as a camp counselor. For example, the counselor can be granted on the days and times of the camp, e.g., Monday, Wednesday and Friday from 8:00 am to 4:00 pm and data access and/or control can be automatically activated during those times and automatically revoked at all other times. The permissions can also require that the counselor be present in a prescribed geographical area, as evidenced, for example, by a location vicinity (i.e., one or more GPS locations) of, e.g., a smartphone or other device of the counselor operating the monitoring application. Similarly, the geographic permissions can also require that a patient device be present in the geographic area and/or be within a certain distance of the caregiver device to also ensure the child is at the camp at the prescribed time. Permissions can be set in this way for any number of caregivers.

In some embodiments, permissions need not be based on both day/time and geographic location, but can be based on only day/time or geographic location. For example, if a child with divorced parents has a set custody schedule, the parents may have differing levels of access and/or control according to the schedule with the parent who has custody of the child at a given day or time having a greater level of access and/or control. Similarly, a greater level of access and/or control may be granted solely on the basis of the child being geographically located at a given parent's house or when the child's device is in a same location or within a given distance of a parent's device, for example. In embodiments, permissions can also be based on other parameters know about a user or a user's device.

Geographical location of a patient's or follower's device can also be used to automatically modify a level of access and functionality for the follower. For example, regulatory or data privacy constraints in a region or country may allow for some functions in some regions that are restricted in others. The system could track a predetermined set of permissions that are enabled for a given region and automatically activate or disable functions based on a location of the patient's and/or follower's device.

The nature of the data that is shared and/or level of control can further be set to varying levels based on the individual receiving the data, including, for example, notifications only, read only access to all data, bolus control only, full pump control, etc. For example, a teacher may only be provided with urgent notifications whereas a school nurse may be given full read only access to all data when the time and geographic conditions for access are satisfied. Similarly, a teacher may not be provided with any ability to program and control device therapy whereas a nurse may be provided with the ability to program and deliver boluses or to fully control all aspects of therapy. In addition, sharing and control can further be based on severity and/or urgency of a notification. For example, a teacher may only be notified of the most severe or urgent notifications whereas a school nurse may be provided with a greater set of notifications or a teacher or school nurse may be provided with expanded control functions based on how urgently a therapy modification is needed.

In some embodiments, data may only be shared and/or control granted when necessary for treatment. For example, data may not be shared when a patient's glucose level is maintained within a predetermined safe range, but a notification may automatically be sent to one or more authorized followers and/or control granted if the patient's glucose level goes lower or higher than the range, the user is exercising or eating requiring a modification to therapy, etc. In some embodiments only the notification may be shared while in other embodiments the out of range notification may trigger an automatic data share for a predetermined period of time. For some followers the notification can only be given if the follower is in a defined geographic area or near the patient device, while some followers may be automatically given the notification regardless of geographic area.

In addition, a follower's schedule can impact the manner in which data and notifications are shared and/or control granted. For example, the system may have access to an electronic calendar of a user from a user's smartphone, tablet, etc. If a user has a meeting, appointment, or other event scheduled, the system can automatically cancel any non-urgent notifications that would occur during the scheduled event and only issue critical notifications that may require immediate attention.

Figure 3:
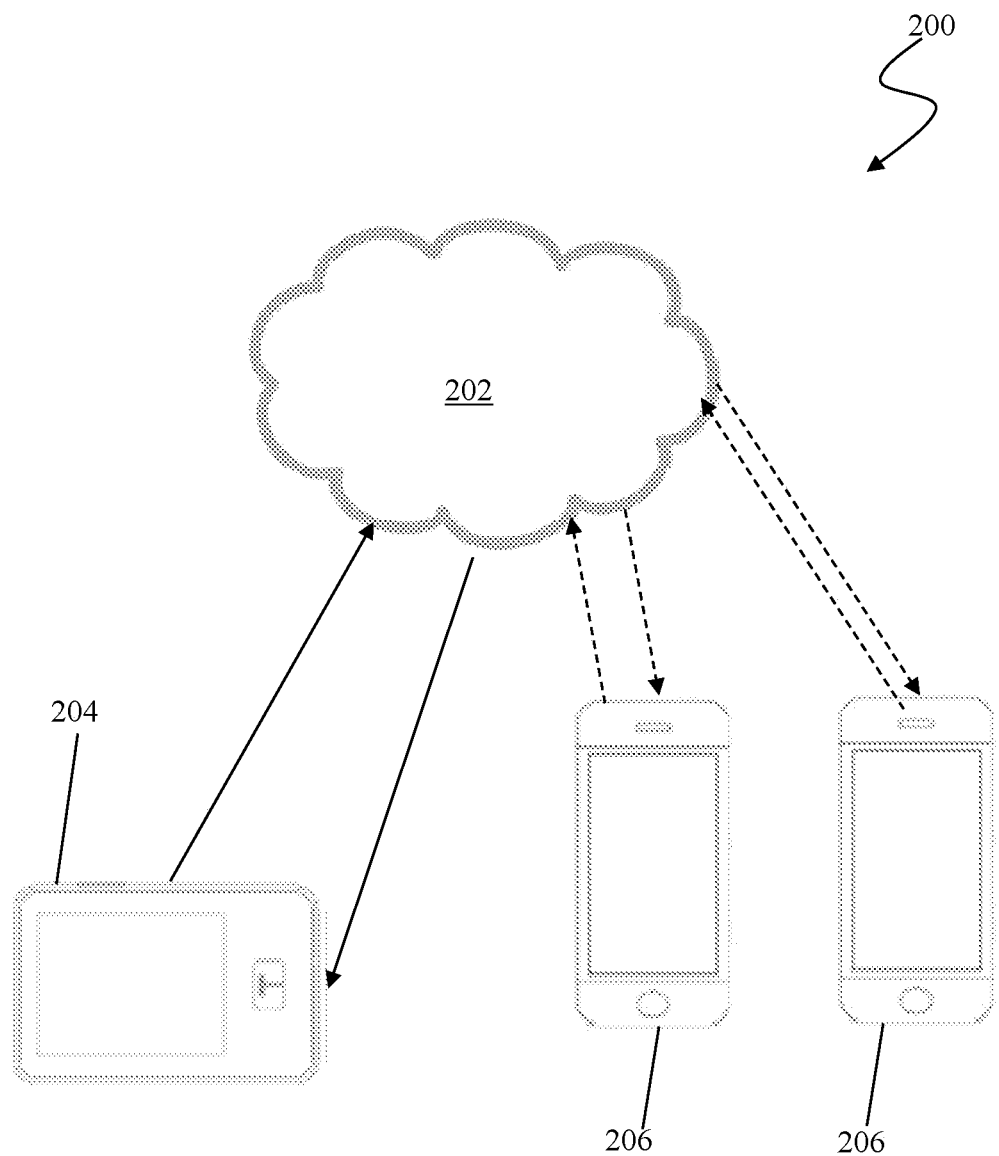
FIG. 3 is a schematic representation of a remote monitoring and/or control system according to an embodiment.
Figure 4:
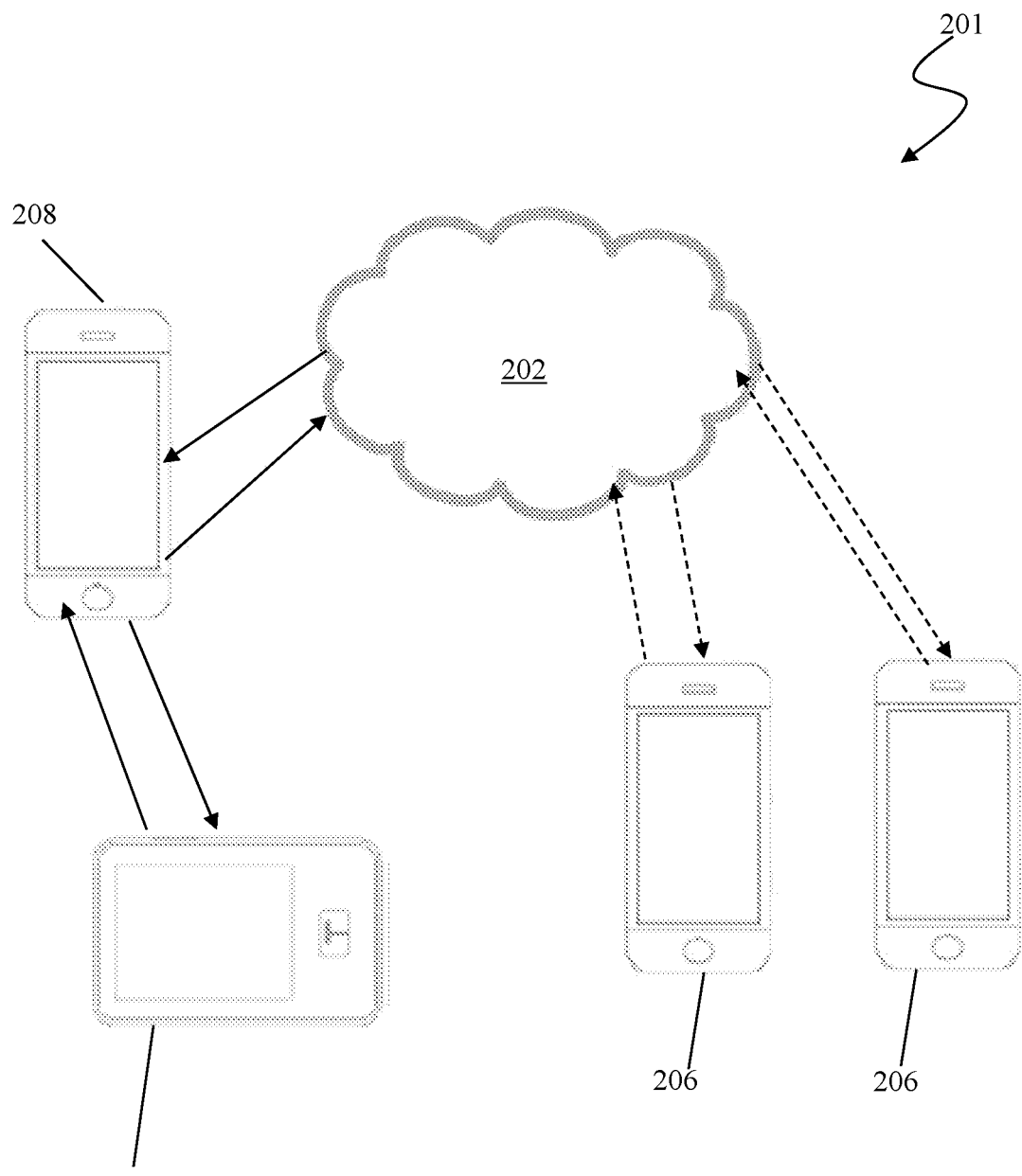
FIG. 4 is a schematic representation of a remote monitoring and/or control system according to an embodiment.

Referring to FIG. 3, a schematic representation of a system 200 for a remote monitoring and/or control architecture is depicted. Remote monitoring architecture can be managed by a remote server 202 via the cloud. A user such as a patient or a parent of a patient can program a set of permissions as disclosed herein for a plurality of followers, which are then stored on the remote server 202. The remote server 202 may continuously or periodically receive data from the patient device 204. The remote server 202 can then automatically grant and revoke access to the data and/or send notifications to a plurality of devices 206 of followers based on the stored sets of permissions. In some embodiments, followers may download and view data and notifications with a software application operating on the followers' devices 206. Alternatively or additionally, devices 206 can be provided with notifications through phone calls, text messages, and/or emails without needing any particular software application. In some examples, a data link can be emailed or texted to a follower with the link providing access only when predefined conditions such as those described herein are met. In some embodiments, control commands for control of patient device 204 can be transmitted to the patient device 204 from the one or more remote devices 206 via the remote server 202. FIG. 4 depicts a similar system 201 in which a remote control device 208, such as a smart phone, that is local to the patient device 204 receives the data from the patient device 204 and facilitates the data transfer to the remote server 202 and/or receives the control commands from the remote server 202 and transmits the commands to the patient device 204.

In some embodiments, rather than all access and/or control being defined from the patient side of the system, followers may be able to directly grant access and/or control to other followers. In some examples, a patient can agree to enable individual or all followers to set permissions for other followers. A patient could also grant access and/or control to an organization such as a school that can set permissions for individuals affiliated with the organization as needed.

The system can also track each follower's use of the application. For example, the system may be able to determine when followers have viewed notifications, accessed patient data, controlled therapy and/or otherwise aided the patient with the patient's therapy based on the shared data or notifications. This record of follower use of the patient's data can then be employed on the patient end of the system to help determine which followers should be granted access and/or control and what level of access should be granted to a given follower. In some embodiments, followers who have not accessed the patient's data or interacted with the application for a given period of time or in response to a given number of notifications can automatically have follower access revoked.

Systems described herein can have additional or alternative uses beyond data and notification sharing and therapy control. For example, retroactive analysis of the geographic and time-based data can provide insights that can be used to make suggestions or predictions for improving the patient's therapy. For example, the system can track abnormal events or other events requiring changes to therapy such as high and low blood glucose excursions including the time such events occur, the location of the user when such events occur and/or which followers are near the user when such events occur. If a user frequently requires changes to therapy at a certain time, in a certain location and/or in the company of a certain follower, the system can suggest that the user modify therapy in those circumstances proactively and/or when the system detects that the user is in a circumstance tied to elevated levels of abnormal events.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10/541,987; 10,569,016; 10,736,037; 10,888,655; 10,994,077; and 11,116,901. commonly owned U.S. Patent Publication Nos. 2009/0287180; 2012/0123230; 2013/0053816; 2014/0276423; 2014/0276569; 2014/0276570; 2018/0071454; 2019/0240398; 2019/0307952; 2020/0114076; 2020/0206420; 2020/0261649; 2020/0306445; 2020/0329433; 2020/0368430; 2020/0372995; 2021/0001044; 2021/0113766; 2021/0154405; and 2021/0353857 and commonly owned U.S. patent application Ser. Nos. 17/368,968; 17/459,129; and Ser. No. 17/517,885.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A server configured to control access to a medical device, comprising:
   a computing device configured to:
      store a set of permissions for one or more followers of a user of a medical device, the set of permissions for each follower of the one or more followers defining one or more times on one or more days during which a follower device of the follower is provided access to the medical device based on one or more other conditions being satisfied;
      determine a location vicinity of the follower device at the times and days when the follower device is provided access to the medical device; and
      automatically provide the follower device with access to the medical device at the times and days if the location vicinity of the follower device is in a predetermined location vicinity stored in the set of permissions, wherein the follower device is restricted from accessing the medical device outside of the times and days.

2. The server of claim 1, wherein the computing device is further configured to determine a location vicinity of the medical device at the times and days when the follower device may be provided access to the medical device.

3. The server of claim 2, wherein the predetermined location vicinity is based on a proximity to the location vicinity of the medical device.

4. The server of claim 2, wherein the access by the follower device is further prevented if the location vicinity of the medical device is not a predetermined location vicinity stored in the set of permissions.

5. The server of claim 1, wherein providing the follower device with access to the medical device includes providing read-only access to data gathered by the medical device.

6. The server of claim 1, wherein providing the follower device with access to the medical device includes enabling the follower device to control medical device functions.

7. The server of claim 6, wherein enabling the follower device to control medical device functions includes enabling the follower device to send medicament delivery commands for delivery of medicament with the medical device.

8. The server of claim 1, wherein providing the follower device with access to the medical device includes providing therapy notifications for the medical device on the follower device.

9. The server of claim 1, wherein the medical device is an insulin pump.

10. The server of claim 1, wherein the follower device is a smartphone.

11. The server of claim 1, the computing device is further configured to automatically prevent access by the follower device to the medical device if the location vicinity of the follower device is not in the predetermined location vicinity or on days and times when the set of permissions does not indicate that the follower device is provided access to the medical device.

* * * * *